(12) United States Patent
Huang

(10) Patent No.: US 6,800,119 B2
(45) Date of Patent: Oct. 5, 2004

(54) APPARATUS FOR GENERATING THE AIR CONDITION RESEMBLING THE AIR ENVIRONMENT IN A FOREST

(75) Inventor: Chün-Hsiang Huang, Chiayi (TW)

(73) Assignee: Chang Gung Biotechnology Co., Ltd., Taipai (TW)

(*) Notice: Subject to any disclaimer, the term of this patent is extended or adjusted under 35 U.S.C. 154(b) by 90 days.

(21) Appl. No.: 10/371,917

(22) Filed: Feb. 21, 2003

(65) Prior Publication Data
US 2004/0163542 A1 Aug. 26, 2004

(51) Int. Cl.[7] ............................ B01D 50/00; A61L 9/14
(52) U.S. Cl. ........................... 96/226; 55/318; 422/123
(58) Field of Search .................... 96/222, 223, 226, 96/227; 55/318, 385.2, 467; 261/115, DIG. 88; 422/123

(56) References Cited

U.S. PATENT DOCUMENTS

| | | | |
|---|---|---|---|
| 4,272,261 A | * | 6/1981 | Lynch et al. ................. 96/222 |
| 5,023,020 A | | 6/1991 | Machida et al. |
| 5,030,253 A | | 7/1991 | Tokuhiro et al. |
| 5,228,235 A | | 7/1993 | Ishimoto |
| 5,656,063 A | | 8/1997 | Hsu |
| 5,702,507 A | | 12/1997 | Wang |
| 5,968,214 A | | 10/1999 | Nagata et al. |
| 2004/0042935 A1 | * | 3/2004 | Guan et al. ................. 422/125 |

FOREIGN PATENT DOCUMENTS

| | | | |
|---|---|---|---|
| JP | 59-212631 A | * | 12/1984 |
| JP | 03-211330 A | * | 9/1991 |
| JP | 09-024294 A | * | 1/1997 |

* cited by examiner

Primary Examiner—Frank M. Lawrence
(74) Attorney, Agent, or Firm—Kenneth P. Glynn, Esq.

(57) ABSTRACT

Fresh and clean air in a forest, which contains abundant anion and phytoncide molecules, relaxes stress and anxiety and helps the metabolism of human body. An apparatus is disclosed in the present invention, which removes the dust particles, chemicals, smelly compounds, etc. in the air. The apparatus further disperses anions and phytoncide molecules in the air to generate an air condition resembling the air environment in a forest, which is fresh, clean and containing substantial amount of anions and phytoncide molecules. The apparatus of the present invention is also very concise and can be used in a small space, such as in an office, a vehicle, etc. The present invention also discloses the design for building the apparatus, which can generate air condition resembling the air environment of a forest, in a compact manner.

20 Claims, 5 Drawing Sheets

A. CONTROL UNIT
B. FAN
C. PHYTONCIDE BOTTLE
D. GAS IONIZER
E. ANION GENERATOR

APPARATUS FOR GENERATING THE AIR CONDITION RESEMBLING THE AIR ENVIRONMENT IN A FOREST

BACKGROUND OF THE INVENTION

1. Field of the Invention

The present invention relates to an apparatus, that cleans air in the ambient space. More particularly, it relates to an air cleaning apparatus, that, in addition to cleaning air, also releases compounds, which are abundant in a forest. The present invention specifically relates to an apparatus, which generates an air condition resembling the air environment in a forest. The apparatus includes an exterior case, which houses a bottle containing phytoncide, a gas ionizer, an anion generator, a filter unit and a fan. The apparatus draws the air from the ambient space, removes the dust particles, chemicals, smelly compounds, etc. from the air, adds anions and phytoncide molecules and disperses the treated air back to the ambient space to generate an air condition, which simulates the air environment in a forest. The present invention also relates to the structural aspects for building the apparatus, which can generate air condition in a close space resembling the air environment of a forest, in a compact manner.

2. Description of the Prior Art

It is known that harmful substances such as fine dust, odor, NOx, etc. adhere to trees in a forest so that these injurious substances are removed from the air. The trees in a forest also discharge plentiful phytoncides molecules, which are hydrocarbons, monoterprene, sesquiterprene, etc. combined with hydroxyl or aldehyde groups, diterprene, phenolic compounds and so on. It is proven that phytoncide molecules emitted by forest trees can help kill bacteria. It is also believed that the phytoncides influence human physiology activity such as mental tranquility, mental composure, awareness, blood pressure, muscular strength, breathing, digestion in the stomach and intestine, urination, sterization, insecticide, etc. and contribute to form a better environment for human life.

The air environment in a forest also contains abundant anions. We feel fresh in the forest, on the seashore or in front of a waterfall or hot spring that is abundant in anions. It is believed that anions in the atmosphere promote cellular metabolism, increase vitality and appetite, purify blood, release anxiety and tension and soothe one's nerves, and is called "vitamin in the air".

Forest bathing, which is a popular exercise in Asian countries, is a means of body sculpting, which includes taking walks and doing aerobic exercises in a forest. Due to all those benefits found naturally in forest areas, forest bathing is extremely good both for people's mental and physical health. When taking forest bathing, it has been found that people's skin temperature can drop by as much as one or two degrees centigrade and their pulses also drop noticeably. The forest bathing is particularly recommended for those with heart diseases and other chronic illnesses.

However, people are busy with work and often do not have the time to travel to the forest to enjoy the air environment in a forest, especially, the inhabitants in the cities. There is a need to provide a compact apparatus, which generates an air condition in the ambient space, such as at home, in an office, an automobile, etc., resembling the air environment in a forest.

U.S. Pat. No. 5,968,214 discloses an air cleaning apparatus, which includes an ozone generator, diffusing plate and active charcoal filter. The ozone generator oxidizes ammonia and acetaldehyde, which are then absorbed and removed by activated charcoal. Ammonia, acetaldehyde and acetic acid, which are bad odor components of cigarette smoke, can be removed sufficiently and actively. The air cleaning apparatus is specifically designed for vehicles only to remove the cigarette smoke and does not generate a pleasant environment similar to the atmosphere in a forest.

U.S. Pat. No. 5,656,063 discloses an air cleaner, which contains an air fan, an air filter, an electric discharge device and an ozone generator. The electric discharge device charged the dust in the air to enhance the precipitation of the dust in the filter. Portion of the filtered air is drawn into a separate chamber where the corona discharge of the ozone generator produces the ozone gas which oxidizes contaminants such as bacteria, chemical compounds or other microorganism suspended in the air.

An air cleaner similar to that of U.S. Pat. No. 5,656,063 is also disclosed in U.S. Pat. No. 5,702,507. The air cleaner pumps the dirty air through dust collecting members with electric discharge rods, a filter plate provided with an odoriferous agent and an ozone tube to terminate the bacteria in the air. Finally, anions pins are adapted to electrify the dust left over in the air so that the dust particles drop onto the ground when the cleaned air is blown out of the case through the exit slots.

In these cases, while harmful matters such as, bacteria, chemicals, smelly compounds, etc., can be removed, volatile organic ingredients, the phytoncides utilized in the present invention, which are naturally discharged from trees in a forest, and act on human physiological activity and release tension and anxiety, are not furnished. In addition, ozone gas is associated with respiratory and other health related problems. Exposure to ozone can result in headaches, throat and nasal dryness, decreased pulmonary function capacity and other respiratory ailments. Thus, the foregoing references are deficient in their teachings and, in some respects, promote unhealthy systems.

U.S. Pat. No. 5,228,235 discloses an apparatus for promoting the generation of volatile organic compounds (phytoncides) from trees. The apparatus contains a plurality of trees in pot trays arranged in intervals, a water supply, an air suction port and an air exhaust system. The trees are rotated to promote the generation of phytoncides. The atmosphere including the phytoncides from the tree is delivered to a living space to activate physiology well being of humans and stabilize one's mind. The apparatus however occupies a large space and is not suitable for a small space such as in an office or a vehicle.

In U.S. Pat. Nos. 5,023,020 and 5,030,253, perfume or aromas are supplied through equipment, such as an air conditioning apparatus or the like, into a room with a view to improve the indoor environment. However, the odor control has involved either masking odors with a heavy perfume or desensitizing the olfactory senses of the persons subject to the smell. The equipment does not provide methods to remove the injurious materials such as chemicals, smelly compounds, microorganism, etc.

It is therefore the object of the present invention to provide a compact air conditioning apparatus, which coordinates phytoncide molecules and ions into an air-cleaning device, to generate a clean air condition in the ambient space simulating the air environment in a forest. People feel fresh as if standing in front of waterfall, walking outdoors after a storm or being in the pine tree woods. The air environment is clean and can release the anxiety and tension.

Another object of the present invention is to provide an air conditioning apparatus, which eliminates the dust particles, bacteria, virus, chemicals and smelly compounds, such as cigarette smoke, in a room and refreshes the air with anions and phytoncide molecules to resemble the air environment in a forest.

A further object of the present invention is to provide a design for building a compact apparatus, which generates an air condition in the ambient space resembling the air environment in a forest, so that it can be easily used in a small space, such as in an office, a vehicle, etc.

The compact apparatus for generating the condition of air, which resembles the environment in a forest, disclosed in the present invention is believed to be neither taught nor render obvious by the prior art.

Notwithstanding the prior art, the present invention is neither taught nor rendered obvious thereby.

SUMMARY OF THE INVENTION

An air conditioning apparatus, which can generate air condition in the surrounding space resembling the air environment of a forest, is disclosed. The air conditioning apparatus has an exterior case, which houses a container containing phytoncides, an air treatment device selected from a gas ionizer, and an anion generator, but preferably both a gas generator and an air ionizer, a filter and an air blow fan. The dirty air in a room is filtered to remove the dust particles, chemicals, smelly compounds, etc. Then phytoncide molecules and anions from the anion generator are added to the clean air and delivered to the ambient. Consequently, the air conditioning apparatus generates the air condition resembling the air in a forest environment, which is abundant in anions and phytoncide molecules. The clean air, which contains anions and phytoncide molecules, in the ambient space helps to release anxiety and tension and contributes to form a better environment for human life. The present invention also provides the design for building the apparatus, which generates air condition in the ambient space resembling the air environment of a forest, in a compact manner.

BRIEF DESCRIPTION OF THE DRAWINGS

The features of the present invention, which are believed to be novel, are set forth with particularity in the appended claims. The invention may best be understood by reference to the following description taken in conjunction with accompanying drawings, wherein like reference numerals identify like elements and wherein:

DETAILED DESCRIPTION OF THE PRESENT INVENTION

Figure 1:
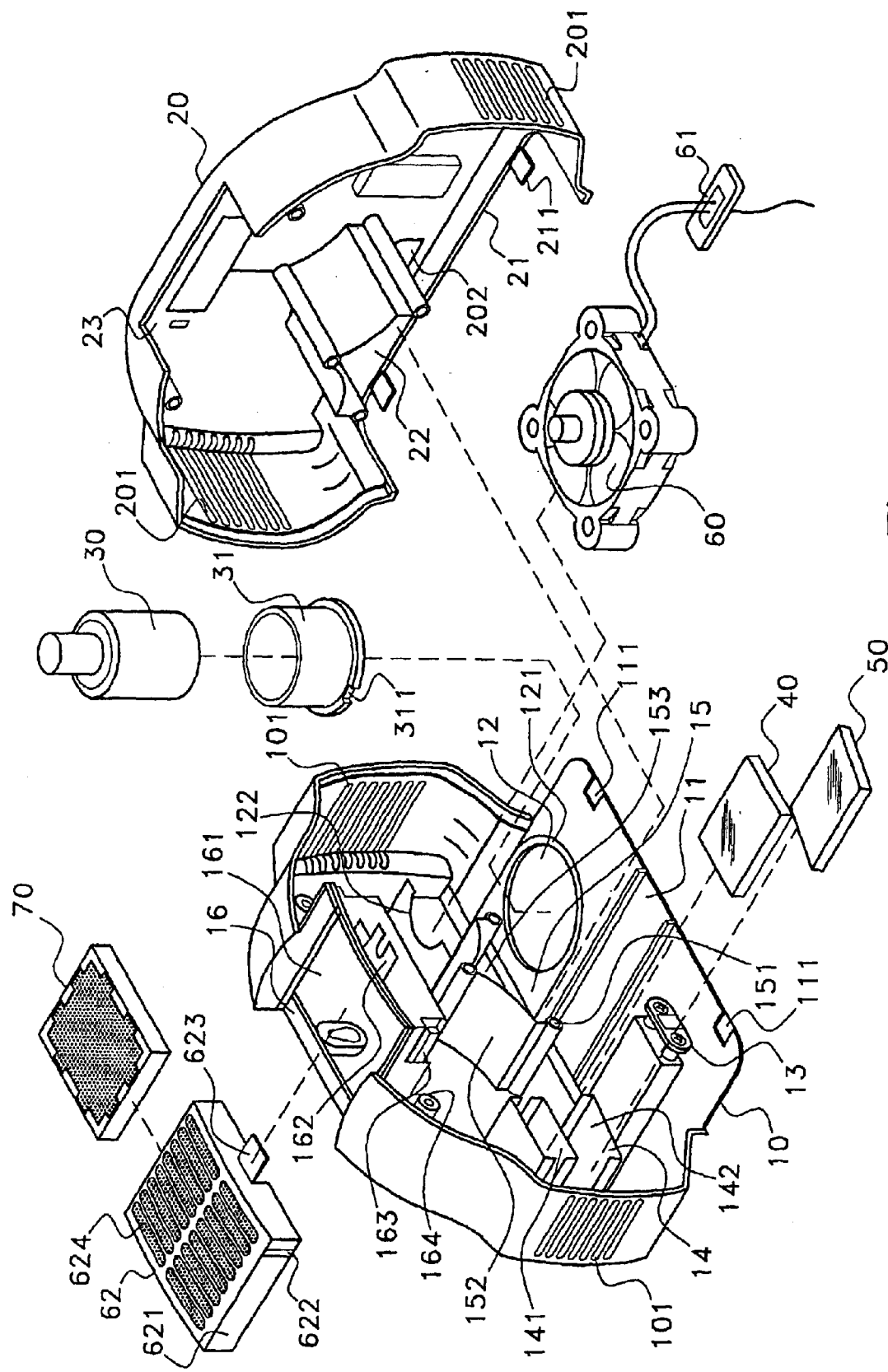
FIG. 1 is a perspective exploded view of the air conditioning apparatus of the present invention, that includes a container containing phytoncide, an anion generator, a fan and an air filter.

Hereinafter, an embodiment of the present invention will be described in detail with reference to the accompanying drawings.

FIGS. 1, 2, 3 and 4 illustrate the present invention apparatus, which generates the air condition resembling the environment in a forest. The apparatus consists of a two-part outer case, a container, in this case a bottle (30) containing phytoncides, a gas ionizer (40), an anion generator (50), a fan (60) and an air filter (70).

The two-part outer case comprises a major case part (10), which includes the base of the case, and a secondary case part (20), which can be attached to the major case part (10) by dowels (211) and holes (111). Venting slots (101) are built in the front and rear sides of the major case part (10). Although the exterior encasement shown in FIG. 1 is one preferred embodiment, other shapes and styles would be within the scope of the present invention. Also, shapes and sizes will vary depending upon application. A portable battery operated device will be small and have provision for battery replacement. An office model will have a bottom that is at least partially flat for resting on a desk or other flat surface. A motor vehicle device will have the shape and presentation for adaptation to a motor vehicle.

Figure 2:
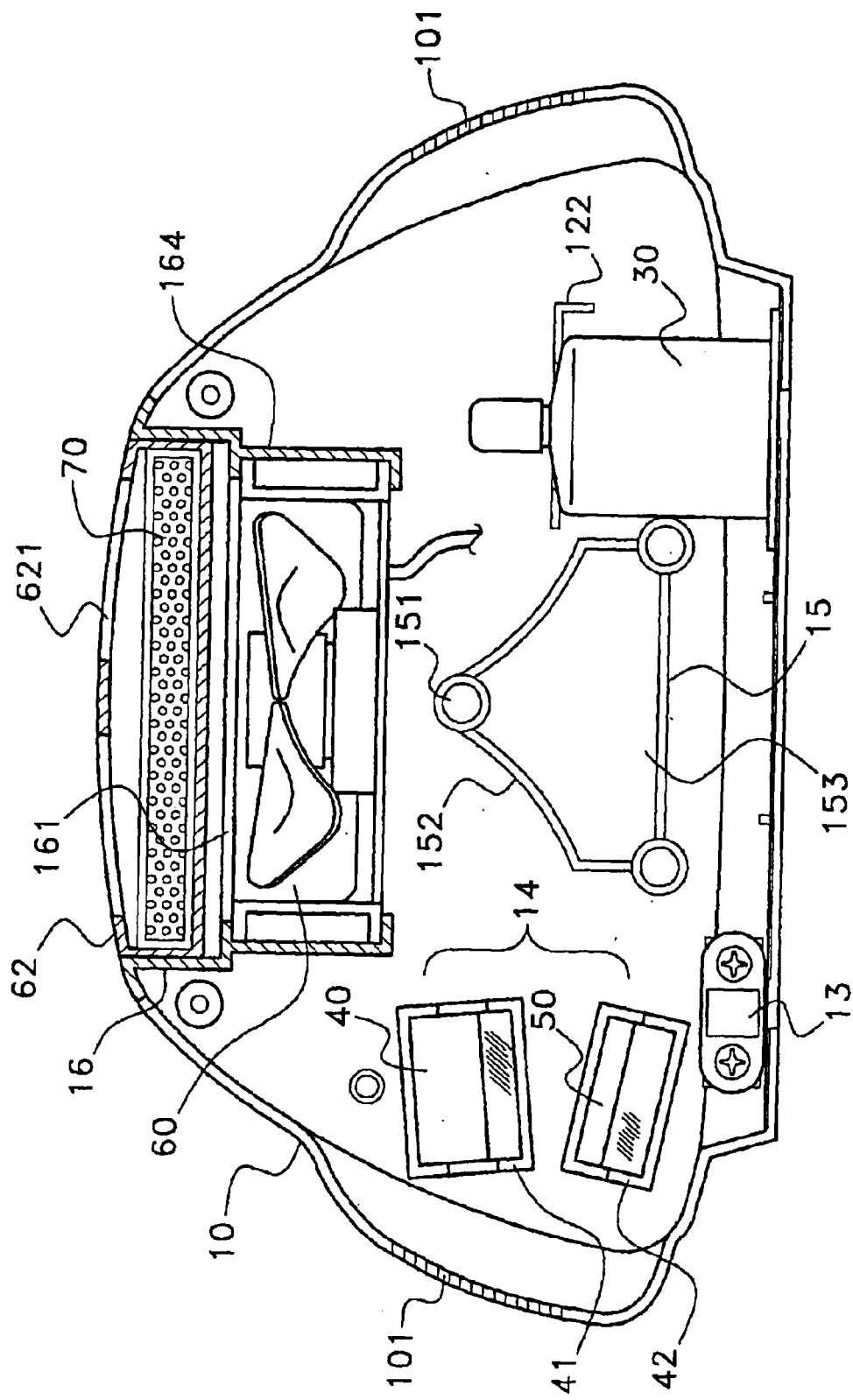
FIG. 2 is a sectional side view of the air conditioning apparatus of the present invention shown above in FIG. 1.

In one side of the base (11) of case part (10) contains a cavity (12), which locks a bottle holder (31). In the other side of the base (11) contains electric socket (13). There are two brackets, (141) and (142), which locate above the electric socket (13). In the center of case part (10), there are three hollow tubes (151), which are attached to the side wall of case part (10) and are interconnected with panels (152). The hollow tubes (151) and panels (152) form an empty space of pentagonal shape (15) as shown in FIGS. 1 and 2. Above the empty space of pentagonal shape (15) and on the top of the case part (10), there is a hole (161), which is of tetragonal shape and is provided with support rim (16) which extends downward to certain extent to form extended edges (163) of the rim (16). Two downwardly extended holders (164) are attached to the opposite extended edges (163) of the rim (16) to form a bracket, which holds the fan (60).

The secondary case part (20) of the outer case contains venting slots (201) in the front and rear sides. In the middle section, there are three hollow tubes, which are interconnected by panels, attached to the wall of the secondary case (20) as shown in FIG. 1. The hollow tubes and panels form a pentagonal empty space (22), which is opposite to the empty space of pentagonal shape (15) in the case part (10). There is a slot (202) on the secondary outer case (20) located beneath the empty space (22). As shown in FIG. 2, the switch (61) of the fan (60) will be affixed to the slot (202) to control the activation of the fan (60).

FIG. 2 illustrates the air inlet at grill cover (62) and the air outlets at the plurality of elongated orifices or slots (101) on the left and right. The defined air path runs from the grill cover (62), through filter (70), past fan (60) and over panel (152), disbursing through slots (101 on the left and right. Other defined air paths may be through the encasement itself or through internal tubing with the various active components (fan anion generator, ionizer, etc.) arranged in parallel or in series. As long as the incoming air passes through the filter and at least a portion of the air is exposed to the other active components, including the phytoncide source, the actual design of the defined air path, given the present disclosure, is a matter of choice and functionality.

The bottle (30) is filled with phytoncide solution and is placed in bottle holder (31), which is subsequently fixed in cavity (12). Phytoncide is a volatile substance, which is contained in very small amounts in the trees and has the function of protecting the trees from the attacks of microorganism. It kills microorganisms, such as staphylococcus, streptococcus, diphtheria, etc. in the surrounding environment. Phytoncides usually occur as complexes with alkaloids, glycoside, organic acid, resins or tannic acid. The volatility of phytoncides varies to a large extent from one another. The phytoncides also exhibit varying pesticidal activities in terms of potency and spectrum and are believed to have positive influence on human physiology activity.

The gas ionizer (40) is placed on the upper bracket (141). The power of the gas ionizer (40) is provided by electric power from socket (13), which is subsequently transformed to higher voltage by transformer (A).

The ionized gases generated from the gas ionizer (40) can kill a wide variety of virus, bacteria and other toxins and eliminate smelly odor and chemicals. It reacts with these compounds, such as phenolics, pesticides, detergents, chemical manufacturing wastes and aromatic (smelly) compounds, and renders them odor free. Since the gas ionizer (40) is operated at much lower voltage than that in an ozone generator, there is no or very little ozone gas generation.

Figure 4:
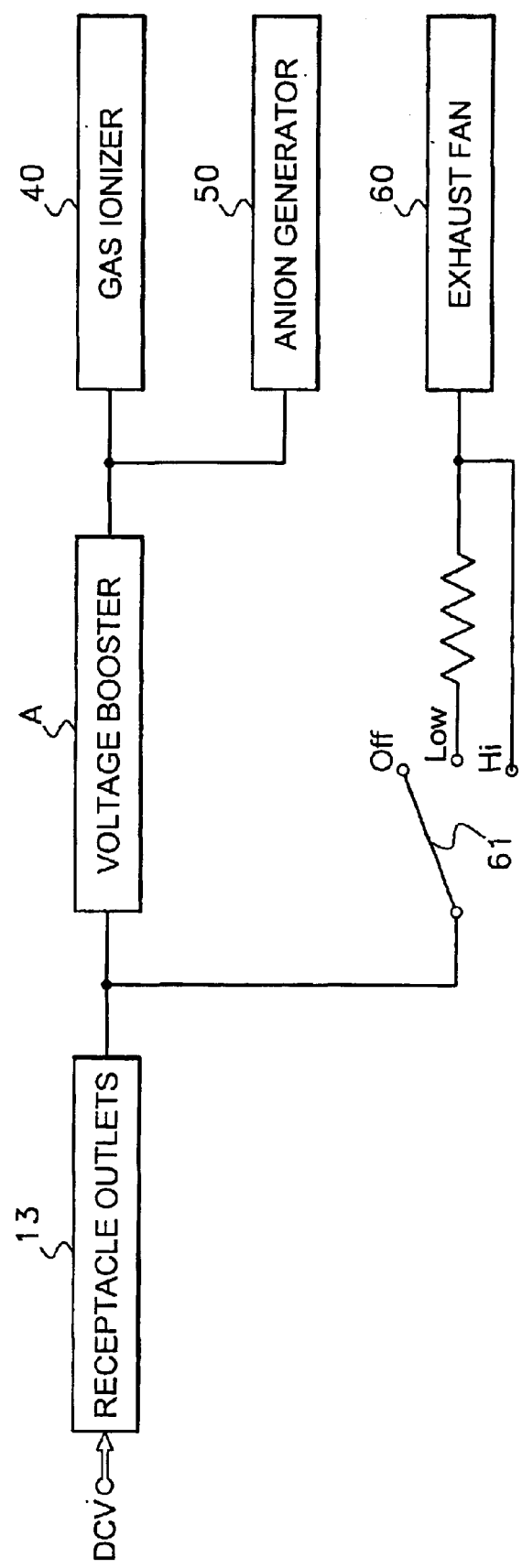
FIG. 4 is a schematic drawing of the circuit in the air conditioning apparatus of the present invention; and, FIG. 5 is a perspective view of a modified air conditioning apparatus of the present invention.

The anion generator locates on the lower racket (142). Anion is an atomic element of negatively charged air particle. As shown in FIG. 4, the power supply to the gas ionizer (40) is from transformer (A), which is provided from the socket (13). Needle shaped device is attached to the anion generator to enhance the electrification of the cleaned air to generate anions.

Figure 3:
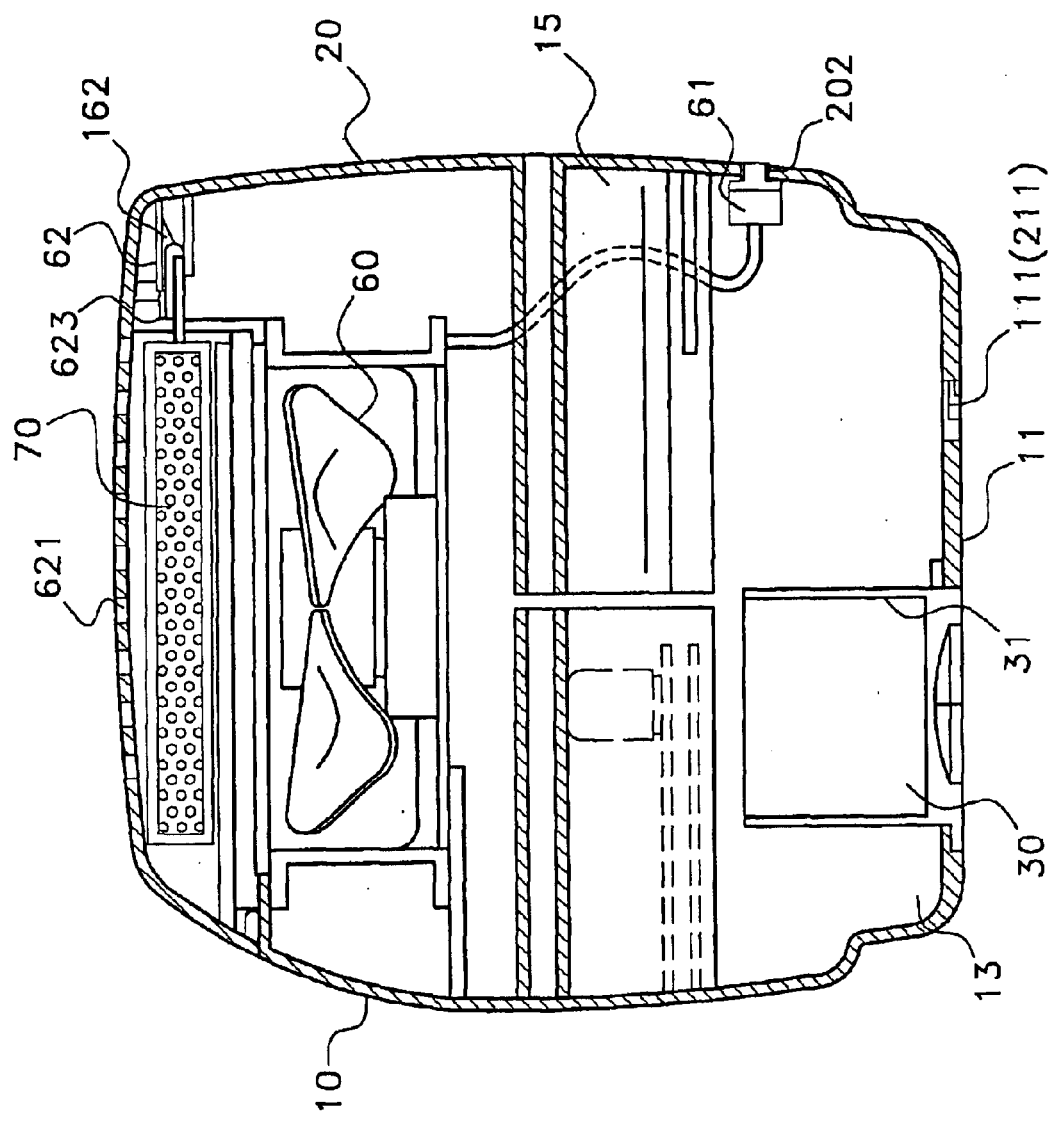
FIG. 3 is a sectional side view from the other direction of the air conditioning apparatus of the present invention shown above in FIG. 1.

The fan (60) is placed above the two holders (164), which are attached to extended edges (163) of the rim (16), occupies the space between the holders (164) and the support rim (16), and locates in the center of hole (161). The fan (60), which uses the power supply directly from the socket (13), is connected to an on-off switch (61), which controls the activation of the fan (60), and subsequently connected to the socket (13). As shown in FIG. 3, the on-off switch (61) is attached to the slot (202) on the secondary case part (20).

Above the fan (60), there is a grill cover (62), which contains a plurality of slots (621), which allow the air to be drawn by the fan (60) into the air conditioning apparatus, and locates above the support rim (16). The grill cover (62) is locked to secondary case part (20) using a latch (623) and a notch (162), which are attached to the grill cover (62) and the case (20), respectively. The filter (70), which removes the dust in the air, is placed in the cavity under the grill cover (62). The filter is preferably an activated carbon filter.

Referring to FIGS. 2 and 4, when the electric socket (13) is connected to a power source, the low voltage power supply is transformed to high voltage electricity by the transformer (A), which is subsequently utilized to activate the gas ionizer (40) and the anion generator (50) to generate ionized gases and anions. The electric power from the socket (13) is also connected to the fan (60) via the on-off switch (61).

When the fan (60) is activated, the air is drawn through a plurality of slots (621) on the grill cover (62) and the filter (70), which removes the dusts or particles in the air. The cleaned air, which is discharged from the fan (60), flows downward and is split into two streams by the edges of the pentagonal shaped space (15). The two cleaned air streams are directed by the two top panels of the pentagonal shape space (15) to the locations of bottle containing phytoncides (30) and gas ionizer (40) and anion generator (50), respectively. The air stream flows over the bottle containing phytoncide and carries the phytoncide molecules through a plurality of slots (101), (201) and disperses the phytoncide molecules in the surrounding space. The other air stream flows past the gas ionizer (40) and anion generator (50). The air stream is treated with ionized gas to kill virus, bacteria and other toxins and to eliminate smelly odors and chemicals then carries and scatters anions in the ambient space by way of slots (101), (201).

As a result, the dust particles, chemicals, smelly compounds, etc. in the air in the close space are removed and replenished with fresh and clean air, which contains anions and phytoncide molecules, by the concise apparatus of the present invention. The fresh and clean air contains abundant anions and phytoncide molecules, which resembles the air environment in a forest and helps to release anxiety and tension. The apparatus of the present invention is also compact and can be used in a small space such as in an automobile. Thus, the present invention apparatus may have a conventional American or European wire and plug, it may have motor vehicle battery connectors. It may have connectors to disposable batteries or rechargeable batteries or connection to another reasonable power source that may be used to provide electric power to the apparatus.

Figure 5:
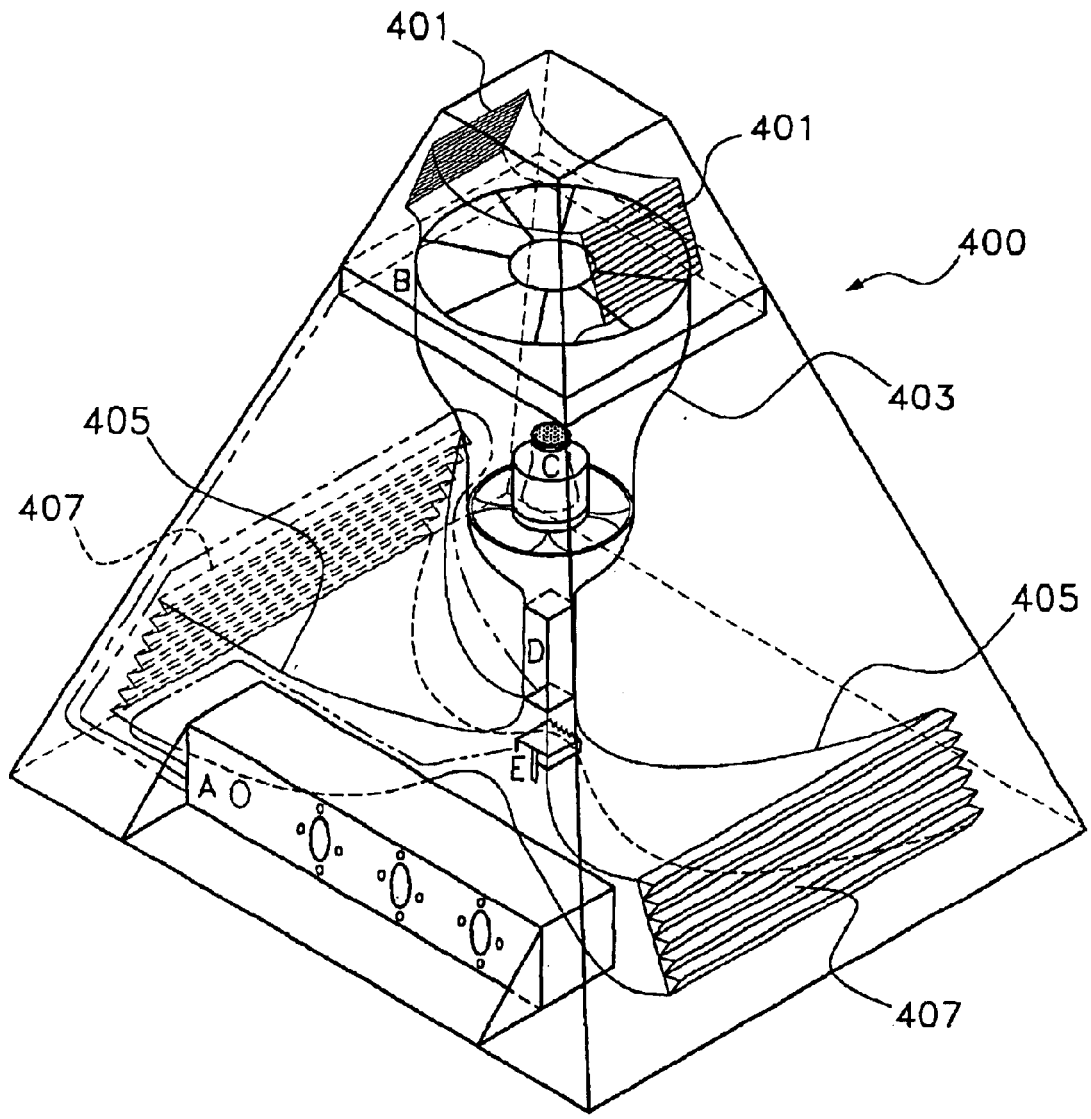

Though the apparatus shown in FIGS. 1 through 4 is shown as a preferred embodiment of the present invention in the previous description, obviously, numerous modifications and variations of the present invention are possible in light of the above teachings. FIG. 5 is a perspective view of another embodiment of a present invention air conditioning apparatus (400), which has the shape of a pyramid and can generate air condition in the surrounding space resembling the air environment of a forest. It includes a control unit A, a fan B, a phytoncide source bottle C, a gas ionizer D and an anion generator E. The air inlet (401) connects to defined air path (403), with in-line components, as shown, and baffles (405), to air outlet (407). It is therefore understood that within the scope of the appended claims, the invention may be practiced otherwise than as specifically described herein.

Obviously, numerous modifications and variations of the present invention are possible in light of the above teachings. It is therefore understood that within the scope of the appended claims, the invention may be practiced otherwise than as specifically described herein.

What is claimed is:

1. An apparatus for cleaning air and generating an air condition that resembles the air environment of a forest, which comprises:
  (a) an exterior encasement for housing active components, said encasement being hollow and having an air inlet, a defined air path, and an air outlet;
  (b) a fan located within said encasement, and positioned within said encasement to draw air into said air inlet, through said defined air path and out of said air outlet;
  (c) an air filter located within said encasement and in said defined air path so that air passes therethrough;
  (d) an air treatment device located within said encasement and in said defined air path, said air treatment device being selected from the group consisting of an anion generator and a gas ionizer;
  (e) a phytoncide source located within said encasement and in said defined air path;
  (f) a power source connection means adapted for connection to or being connected to a power source, and being connected to said fan, and said air treatment device; and
  (g) control means connected to said power source connection for controlling power to said fan, and said air treatment device.

2. The apparatus of claim 1 wherein said air inlet includes a grill cover.

3. The apparatus of claim 2 wherein said grill cover is removable, said filter is located adjacent said grill cover and said filter is removable.

4. The apparatus of claim 1 wherein said phytoncide source is a container containing phytoncide.

5. The apparatus of claim 1 wherein said phytoncide source is removable and replenishable.

6. The apparatus of claim 1 wherein said power source connection is selected from the group consisting an AC outlet plug, a motor vehicle power supply connector and a replaceable battery connector.

7. The apparatus of claim 1 wherein said exterior encasement is an assemblage of a plurality of interconnected sections.

8. The apparatus of claim 1 wherein said air outlet is a plurality of elongated orifices located on said encasement at an end of said defined air path.

9. The apparatus of claim 1 wherein said exterior encasement has a base having a flat portion for resting on a flat surface.

10. The apparatus of claim 9 wherein said exterior encasement has a generally pyramidal exterior shape.

11. An apparatus for cleaning air and generating an air condition that resembles the air environment of a forest, which comprises:

(a) an exterior encasement for housing active components, said encasement being hollow and having an air inlet, a defined air path, and an air outlet;

(b) a fan located within said encasement, and position within said encasement to draw air into said air inlet, through said defined air path and out of said air outlet;

(c) an air filter located within said encasement and in said defined air path so that air passes therethrough;

(d) a gas ionizer located within said encasement and in said defined air path;

(e) an anion generator located within said encasement and in said defined air path;

(f) a phytoncide source located within said encasement and in said defined air path;

(g) a power source connection means adapted for connection to or being connected to a power source, and being connected to said fan, said gas ionizer and said anion generator; and (h) control means connected to said power source connection for controlling power to said fan, said gas ionizer and said anion generator.

12. The apparatus of claim 11 wherein said air inlet includes a grill cover.

13. The apparatus of claim 12 wherein said grill cover is removable, said filter is located adjacent said grill cover and said filter is removable.

14. The apparatus of claim 11 wherein said phytoncide source is a container containing phytoncide.

15. The apparatus of claim 11 wherein said phytoncide source is removable and replenishable.

16. The apparatus of claim 11 wherein said power source connection is selected from the group consisting an AC outlet plug, a motor vehicle power supply connector and a replaceable battery connector.

17. The apparatus of claim 11 wherein said exterior encasement is an assemblage of a plurality of interconnected sections.

18. The apparatus of claim 11 wherein said air outlet is a plurality of elongated orifices located on said encasement at an end of said defined air path.

19. The apparatus of claim 11 wherein said exterior encasement has a base having a flat portion for resting on a flat surface.

20. The apparatus of claim 19 wherein said exterior encasement has a generally pyramidal exterior shape.

* * * * *